(12) United States Patent
Saggers

(10) Patent No.: US 10,206,812 B2
(45) Date of Patent: Feb. 19, 2019

(54) THERMAL PACK FOR THERAPEUTIC TREATMENT AND INSERT THEREFOR

(75) Inventor: Mike Saggers, Bedfordshire (GB)

(73) Assignee: GIOCO LIMITED, Barton-le-Clay, Bedfordshire (GB)

(*) Notice: Subject to any disclaimer, the term of this patent is extended or adjusted under 35 U.S.C. 154(b) by 1114 days.

(21) Appl. No.: 14/118,860

(22) PCT Filed: May 21, 2012

(86) PCT No.: PCT/GB2012/051149
§ 371 (c)(1),
(2), (4) Date: Feb. 18, 2014

(87) PCT Pub. No.: WO2012/156761
PCT Pub. Date: Nov. 22, 2012

(65) Prior Publication Data
US 2014/0155964 A1     Jun. 5, 2014

(30) Foreign Application Priority Data
May 19, 2011    (GB) .................................. 1108377.1

(51) Int. Cl.
*A61F 7/02*        (2006.01)
*A61F 7/00*        (2006.01)

(52) U.S. Cl.
CPC .............. *A61F 7/02* (2013.01); *A61F 7/0097* (2013.01); *A61F 2007/0054* (2013.01); *A61F 2007/0056* (2013.01); *A61F 2007/0273* (2013.01)

(58) Field of Classification Search
CPC combination set(s) only.
See application file for complete search history.

(56) References Cited

U.S. PATENT DOCUMENTS

| 4,108,146 A | 8/1978 | Golden |
| 4,821,354 A * | 4/1989 | Little ..................... A47C 1/143 138/103 |

(Continued)

FOREIGN PATENT DOCUMENTS

WO       2012/066339 A2     5/2012

OTHER PUBLICATIONS

International Search Report and Written Opinion, in corresponding International application No. PCT/GB2012/051149, International filing date Nov. 17, 2011.

(Continued)

*Primary Examiner* — Joseph Stoklosa
*Assistant Examiner* — Adam Avigan
(74) *Attorney, Agent, or Firm* — Donald E. Stout; Stout, Uxa & Buyan, LLP

(57) ABSTRACT

A thermal pack (10) for therapeutic treatment of a mammal that includes a bladder (12, 4) and a separator element insert (22). The bladder (12, 14) is formed of a pair of superposed sheets (12, 14) of flexible, heat conductive liquid impermeable polyurethane material and includes an inlet (18) and an outlet (20). The sheets (12, 14) are welded together at a central spine (17) and along a series of branches (16) so as to provide a turning, tortuous fluid passageway therein. The separator element insert (22) is received within the fluid passageway and provides a fluid conveying track that extends throughout the fluid passageway from the inlet (18) to the outlet (19) to maintain the sheets (12, 14) in spaced apart relationship to mitigate restrictions in fluid flow when the pack (10) is flexed out of the plane of the sheets (12, 14). The separator element insert (22) includes a series of deflector ribs (36, 38, 40, 42, 44) along the fluid conveying track that deflect fluid flow away from the separator element insert (Continued)

(22) and into the fluid passage way along at each turn of the fluid passageway.

20 Claims, 3 Drawing Sheets

(56) References Cited

U.S. PATENT DOCUMENTS

| | | |
|---|---|---|
| 5,330,519 A | 7/1994 | Mason |
| 5,383,919 A | 1/1995 | Kelly et al. |
| 6,197,045 B1 | 3/2001 | Carson |
| 6,238,427 B1 | 5/2001 | Matta |
| 7,204,041 B1 * | 4/2007 | Bailey, Sr. ........... A43B 3/0005 36/1 |
| 8,613,762 B2 | 12/2013 | Bledsoe |
| 2003/0019476 A1 | 1/2003 | Chambers |
| 2012/0172957 A1 * | 7/2012 | Dewaegenaere ......... A61F 7/02 607/104 |
| 2014/0222121 A1 | 8/2014 | Spence |
| 2014/0243939 A1 | 8/2014 | Lowe |
| 2014/0277302 A1 | 9/2014 | Weber |
| 2015/0190274 A1 | 7/2015 | Landy |
| 2016/0128865 A1 | 5/2016 | Lowe |
| 2016/0166428 A1 | 6/2016 | Hilton |

OTHER PUBLICATIONS

Related U.S. Appl. No. 13/988,145, filed May 17, 2013.

* cited by examiner

THERMAL PACK FOR THERAPEUTIC TREATMENT AND INSERT THEREFOR

This application claims priority to PCT International Application No. PCT/GB2012/051149, having an international filing date of May 21, 2012, and entitled Thermal Pack for Therapeutic Treatment and Insert Therefor, which in turn claims priority to Great Britain Application No. 1108377.1, filed on May 19, 2011. Both of the foregoing applications are herein expressly incorporated by reference, in their entirety.

This invention relates to a therapeutic device for external application to a mammal and more particularly to a therapeutic device for the heating, or cooling of a selected area of a mammalian body, especially, but not exclusively, of the human body. The invention also relates to an insert for such a device, e.g. an anti-occlusion insert for incorporation within such a thermal pack.

The device takes the form of a heat conductive bladder that will conform to various contours of the body to aid in the therapeutic treatment of sports injuries and other forms of trauma, to relieve post operative pain, and to control swelling, bruising and engorgement.

Devices for applying heat or cold, such as a heat pack or cold pack, to areas of the human body are well known. Known ice packs, for example, may comprise sealed enclosures which contain particulate matter, water, glycol, a mixture thereof or other fluid medium which is pre-chilled in a refrigerating device and the chilled or, in some cases, frozen pack then applied to an area of the skin of a human or other mammalian body to treat and/or control inflammation, bruising and/or infection and to promote healing and/or to relieve pain.

However, such cold pack devices have disadvantageous aspects and are of limited use since they tend to be too intense in their cooling effect when first applied and have been found to induce frostbite. Moreover, the ice packs lose much of their effectiveness because they warm up rather quickly through heat exchange with the body, thereby providing a constantly changing temperature at the areas of contact. Other devices in which the heat exchange with the body, and hence the therapeutic treatment, is prolonged are known. These other known devices with prolonged effectiveness include flexible sealed enclosures through which a chilled or heated fluid medium is caused to flow by pumping the fluid medium through the device. Such devices are known in the art by various descriptions such as garments, bladders, bandages, pads, wraps, cuffs and the like, but in each case the device generally comprises a flexible sealed enclosure (hereinafter a 'thermal pack') which can be applied and secured to an area of the body to be treated. A chilled or heated fluid medium can be caused to flow through the enclosure to provide a cooling or heated therapeutic treatment.

In relation specifically to cold therapy treatment, or cryotherapy as it is known, equipment to circulate fluid through a thermal pack generally comprises a chiller unit supplying cold fluid to a thermal pack by way of circulation through insulated hoses. More simplistic (and cheaper) systems operate by raising and lowering a water-ice tank to fill and then empty a thermal pack via a single hose. These systems should not be confused with the cold packs referred to above such as gel filled flexible enclosures which are placed in a freezer and then applied to the treatment area of the body without any circulation or ingress or egress of fluid relative to the pack.

An effective therapy requires the maintenance of a constant even temperature at a desirable level over the treatment area. The various cooling techniques presently in use fail satisfactorily to maintain a constant temperature on the desired body areas. In addition to the requirement of maintaining a constant temperature on the selected areas, there is also a need for a thermal pack that will comfortably and securely fit the contours of the area being treated as well as a need for providing portability of the cooling (or heating) unit. Application of the thermal pack to an area of the body, e.g. the knee, causes it to fold and crease creating restrictions which reduce or cut off the flow of fluid and causes "dead areas" with little or no fluid movement which results in loss of temperature control at that or those point(s). Accordingly, there is a need for ensuring uninterrupted flow and dispersion of fluid over the complete surface of the thermal pack.

EP 2 269 546 A1 discloses an occlusion resistant and/or multilayer treatment pad for thermal treatment of a human or animal body. It includes a thermal pad which comprises two outer layers forming a fluid communication channel therebetween and an anti-occlusion body encapsulated by the outer layers. However, in this known construction the anti-occlusion body is not in the form of a fluid conveying track but, on the contrary, comprises material which inhibits fluid flow such as an additional layer of foam or filter material or mesh fabric or non-woven fabric or web.

One aspect of the present invention provides a thermal pack for therapeutic treatment of a mammal, the pack comprising a flexible, heat conductive liquid impermeable bladder with ingress and egress means for the ingress and egress of a fluid medium, the bladder comprising a pair of superposed sheets secured together so as to provide a fluid passageway, e.g. a turning fluid passageway, within the bladder and a separator element within the fluid passageway to mitigate restrictions in the fluid flow through the passageway when the pack is flexed, in use, out of the plane of the superposed sheets, wherein the separator element comprises a fluid conveying track that extends throughout the fluid passageway, e.g. from the inlet to the outlet, between the superposed sheets and maintains the superposed sheets in spaced apart relationship at least in the vicinity of the track, and wherein the fluid conveying track comprises elements or deflectors which disrupt laminar flow along the fluid conveying track and/or deflect fluid in at least one of the turns of the fluid passageway.

The ingress means is preferably comprises an inlet and/or the egress means preferably comprises an outlet. The fluid passageway may be provided by one or more portions or areas or zones of the superposed sheets that are secured, preferably welded, together, for example around their peripheries and/or along a central spine and/or along one or more branches. The central spine and/or one or more branches may comprise one end or free end that terminates at a central or intermediate portion of the superposed sheets, for example to provide a turn in the fluid passageway, e.g. about the end or free end. In a preferred embodiment, the superposed sheets are substantially in the shape of an H and/or are secured or welded together around their peripheries and along a central spine and four branches extending from, e.g. substantially perpendicularly from, the central spine to define a tortuous path for the fluid passageway.

Another aspect of the invention provides an insert or separator element for use in a thermal pack, e.g. as described above. The insert or separator element may comprise a fluid conveying track and/or one or more deflectors, e.g. along the fluid conveying track, for example which deflectors are configured to deflect, in use, fluid flow away from the separator element and/or into the fluid passageway along at least one of the turns of the fluid passageway Preferably, at least one deflector comprises a turn guide, e.g. that directs fluid flow around the at least one turn of the fluid passageway. More preferably, the turn guide is located adjacent an internal portion of the turn of the fluid passageway. The separator element may further comprise a central rib, e.g. that may cooperate with the turn guide such as to provide a curved fluid channel for fluid to flow therein and around the curve of the fluid passageway.

At least some of the elements may be shaped and/or orientated to cause fluid flow along the fluid conveying track to be deflected into the fluid passageway, e.g. into the centre thereof.

The separator element or fluid conveying track preferably comprises a strip, e.g. a tortuous strip, of flexible material having a base and wherein said elements comprise ribs which are upstanding from the base. The separator element may comprise ribs on each of the main surfaces of the base, for example wherein some ribs extend upwardly from the base, e.g. an upper surface of the base, and/or some ribs extend downwardly from the base, e.g. a lower surface of the base.

The fluid conveying track may include one or more continuous channels, each of which may extend along at least a part of the track, for example at or through or about a curve or turn of the fluid passageway. Preferably, in some constructions a single channel extends along at least a part of the centre of the track. It also is preferably in the, some or other constructions that a single channel extends along at least a part of the track between the centre and one edge thereof.

The fluid conveying track may be symmetrical about its longitudinal centre line along a portion thereof. Additionally or alternatively, the fluid conveying track may be asymmetrical along the at least one turning portion thereof.

At least some of the ribs may be arcuate in form. In constructions where arcuate ribs are provided, the arcuate ribs may be disposed adjacent to the edges of the track and wherein a centrally extending rib is disposed between spaced pairs of arcuate ribs and wherein the each pair of arcuate ribs together with the centrally extending rib creates restricted passages at spaced locations along the track. Moreover, the arcuate ribs may be orientated to deflect the flow of fluid into the fluid passageway.

Another aspect of the invention provides a fluid conveying track for a thermal pack as described above.

Thermal packs and anti-occlusion inserts therefor, embodying the invention will now be described, by way of example, with reference to the accompanying drawings, in which.

Figure 1:
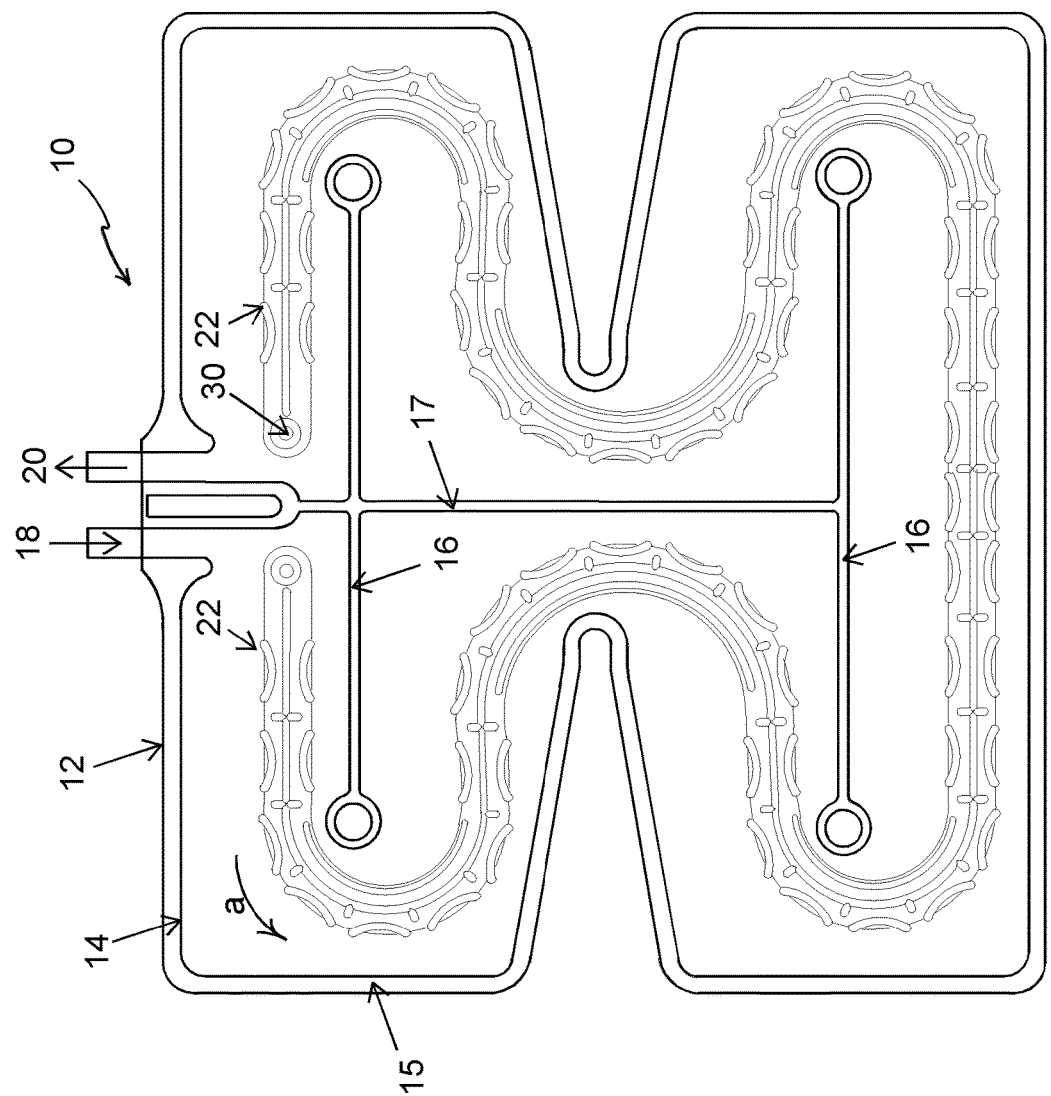
FIG. 1 is a plan view of a thermal pack according to the invention, shown in flat unfolded condition.

Referring first to FIG. 1 of the drawings, there is shown a thermal pack 10 which comprises a sealed bladder of heat conducting and water impermeable material. The pack 10 includes a back sheet 12 and a front sheet 14, which are secured in superposed relationship and preferably are welded together around their peripheries 15 and also preferably in selected areas 16 in the body of the pack which includes a central spine 17. The front sheet and the back sheet are formed from polyurethane. In this particular embodiment the thermal pack is generally in the form of an "H" comprising a double set of wings, and which is symmetrical about the central spine. The pack is shaped to be particularly useful for the therapeutic treatment of, for example, a knee, elbow or ankle.

The therapeutic pack 10 is able to contain and convey fluid supplied to the unwelded areas of the interior of the pack. An inlet nozzle 18 welded between the sheets of the pack supplies fluid to the wings of the pack so that fluid can circulate between the front sheet and the back sheet of the pack and be discharged from an exit nozzle 20 which is welded in position alongside the inlet nozzle 18. The unwelded areas of the superposed sheets provide a continuous fluid passageway through the thermal pack, and the fluid flow is shown by arrows 'a'.

In order to ensure uninterrupted flow of fluid through the pack, one or more anti-occlusion inserts 22 are encapsulated within the fluid passageway of the pack and therefore disposed between the front sheet and the back sheet. In this particular embodiment of the invention, the anti-occlusion insert comprises a continuous tortuous fluid conveying track which is disposed between the front and back sheets on either side of the central spine 17 of the pack and meanders around the welded areas 16. The track is formed from relatively stiff (mouldable plastics) material as compared to the front and back sheets and comprises numerous elements which disrupt laminar flow along the track. In this embodiment the track is continuous throughout the pack and is held in position by welded studs 30 external to the main outer perimeter of the pack. However, the various elements of the track, as described in more detail below, not only disrupt the laminar flow of fluid along the track but also divert the flow into the fluid passageway between the sheets of the pack. The track, which is a separate insert, acts as a diffuser. Thus, the fluid conveying track, not only maintains a spaced apart relationship between the front sheet and the back sheet 12, 14 at least in the vicinity of the track but also provides a fluid diffusing 'highway' running through the pack.

The track insert is connected to the front or back sheet of the pack by a number of studs 30 provided adjacent the inlet and outlet nozzles, although such a connection or indeed any connection is not essential. Thus the track may be unattached to either one of the sheets of the pack but merely encapsulated within the pack.

The track may take numerous forms, but although it carries fluid itself, disrupts laminar flow and acts as a fluid diffuser, the track also must function so as to maintain fluid flow through the pack between the front and back sheets when the pack is in use. In use, the thermal pack is flexed out of the plane of the superposed sheets to bring it into a folded and compressed condition around the contours of an area of the body such as for example, a knee, elbow, ankle or shoulder.

Figure 2:
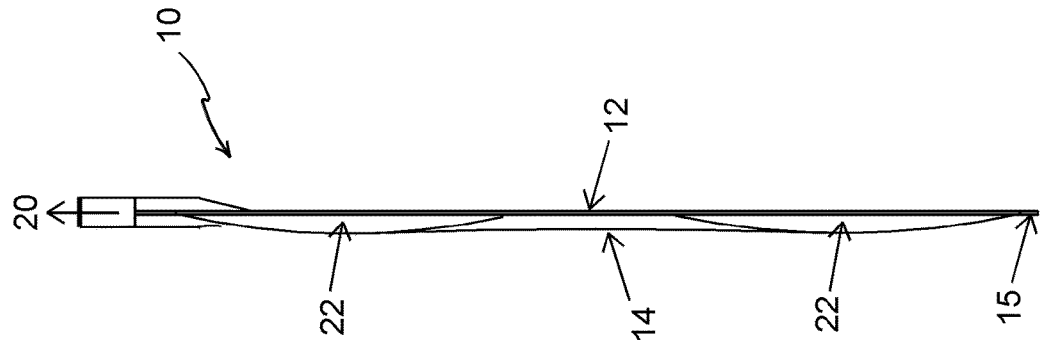
FIG. 2 is a side view of a thermal pack.

Referring now to FIG. 2 of the drawings, a side view of a thermal pack 10 is shown in flat unfolded condition. The pack includes a back sheet 12 and a front sheet 14, which are secured in superposed relationship and preferably are welded together around their peripheries 15. The exit nozzle 20 through which fluid can be discharged from the pack is welded in position.

In this particular embodiment the thermal pack is generally in form of an "H" comprising a double set of wings. The anti-occlusion inserts 22 are encapsulated within the fluid passageway of the wings in order to ensure uninterrupted flow of fluid through the pack.

Figure 3:
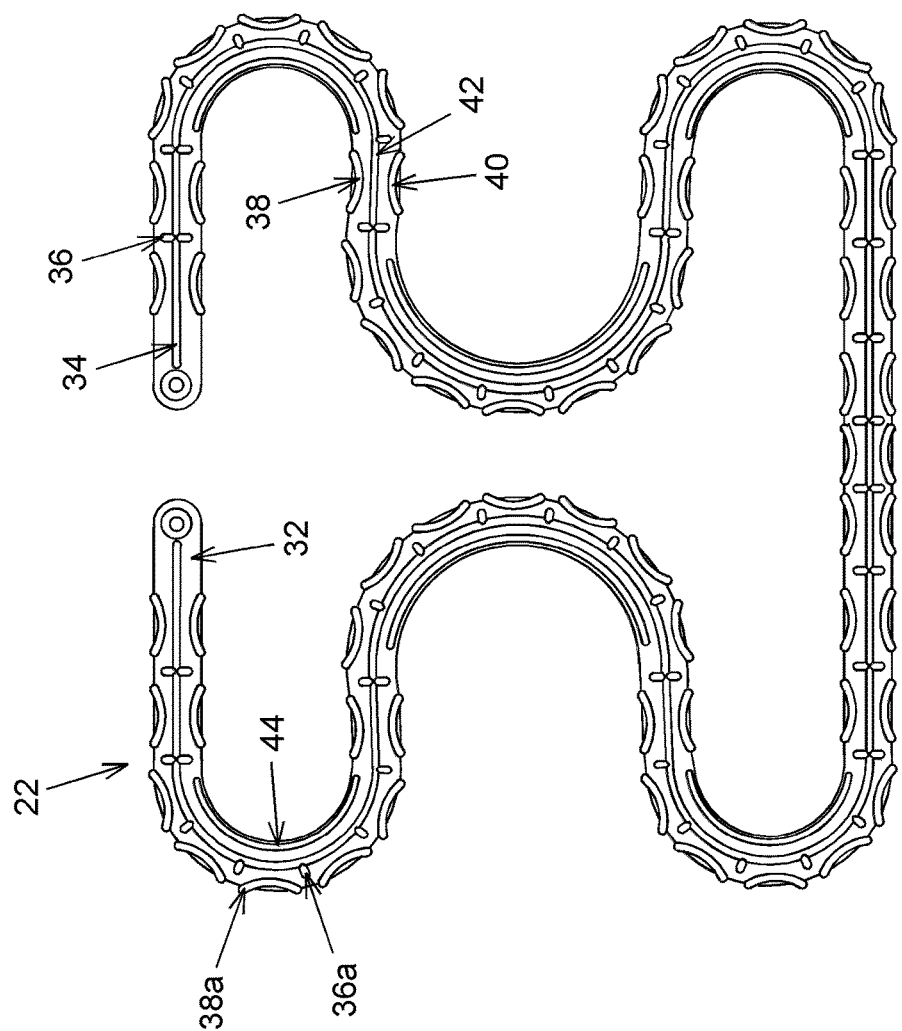
FIG. 3 is a plan view of an anti-occlusion insert, arranged as if within a thermal pack.
Figure 4F:
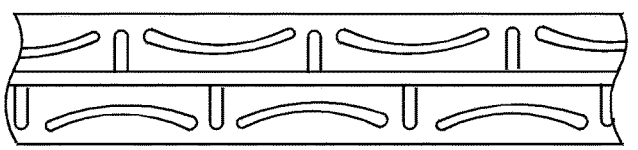
FIG. 4 shows a variety of separator elements which may be incorporated in a thermal pack according to the invention.
Figure 4E:
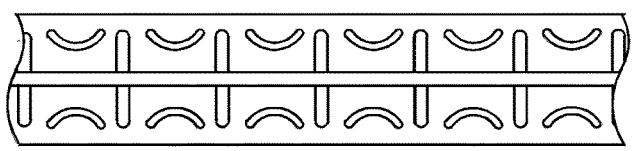
Figure 4D:
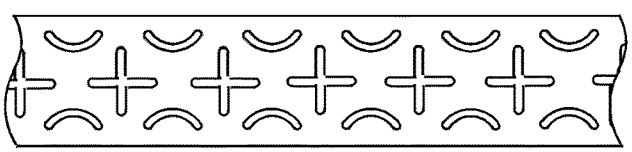
Figure 4C:
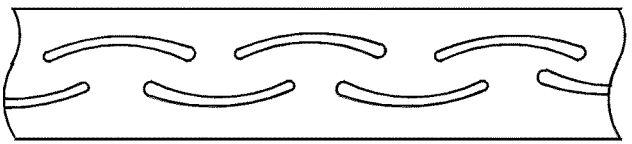
Figure 4B:
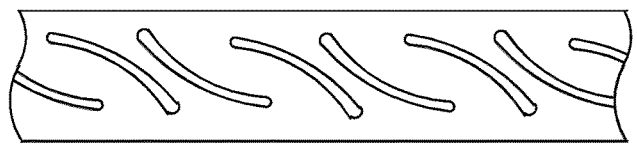
Figure 4A:
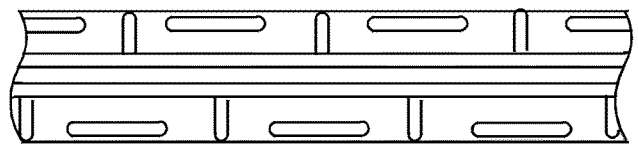

Referring now to FIG. 3 of the drawings, an anti-occlusion insert is shown which comprises the track 22 which is formed with a number of flow regulating elements. The track 22 comprises a base 32 from which integral flow regulating elements are upstanding. The main elements in this particular embodiment comprise a central rib 34 which is coextensive with the track. In relatively straight sections of the track, the central rib is interrupted by spaced cross-ribs 36 which are perpendicular to the central rib. A pair of arcuate ribs 38, 40 are disposed, one on either side of the central rib between each successive cross-rib. The arcuate ribs are spaced from the central rib adjacent the edges of the track. Each pair of arcuate ribs 38, 40 provides a restricted channel 42 within the track and the general arrangement of the upstanding elements is such as to deflect and diffuse the fluid flow away from the track and into the fluid passageway between the top and bottom sheets of the pack.

In curved sections of the track, the central rib 34 is accompanied by a parallel curved rib or turn guide 44 which together with the central rib, provides a curved fluid channel 45 for fluid flow around the inside curve of the track. On the outside face of the central rib 34, the track is formed with a series of spaced cross-ribs 36a which extend outwardly towards, but stopping short of, the adjacent edge of the track. Between each pair of cross-ribs 36a, the track is formed with an arcuate rib 38a of similar form to the arcuate ribs 38, 40 referred to above. The general arrangement of the cross and arcuate ribs is such as to deflect and diffuse the fluid flow away from the track and into the fluid passageway between the top and bottom sheets of the pack.

The track element may however comprise a multiplicity of differing arrangements of separating elements of various sizes, shapes and dispositions between the sheets, as shown by way of example in FIG. 4 of the drawings in examples 4a, 4b, 4c, 4d and 4e. In some cases the separator device may comprise a plurality of discrete "islands" between the front and back sheets of the pack which are sufficient in number to maintain substantially uninterrupted flow of the fluid medium through the thermal pack no matter what its configuration, but not so numerous as to inhibit the effective therapeutic treatment by virtue of the presence of the separator "islands" causing reduction in heat transfer between the thermal pack and the treatment area.

The therapeutic treatment envisioned by the preferred embodiment of the present invention may also be administered together with intermittent compression therapy which itself is well known in the art. The combined therapy helps to reduce initial swelling and continues to reduce swelling by forcing fluids into the lymphatic system, which in turn lowers the pressure on the limb and promotes fluid reabsorption. The therapy is also of help in the restoration of an oxygenated blood flow to increase healing.

The invention claimed is:

1. A thermal pack for therapeutic treatment of a mammal, the pack comprising:
   a flexible, heat conductive liquid impermeable bladder and
   a separator element,
   the bladder comprising an inlet, an outlet and a pair of superposed sheets secured together so as to provide a fluid passageway having a plurality of turns therein,
   the separator element being received within the fluid passageway and comprising a fluid conveying track that extends throughout the fluid passageway substantially from the inlet to the outlet to maintain the superposed sheets in spaced apart relationship at least in the vicinity of the track to mitigate restrictions in the fluid flow through the passageway when the pack is flexed, in use, out of the plane of the superposed sheets, wherein the separator element comprises a tortuous strip of flexible material having a base and ribs which are spaced from one another in a fluid flow direction, which are upstanding from the base and which disrupt laminar flow along the fluid conveying track and deflect fluid flow away from the fluid conveying track and into the fluid passageway along at least one of the turns of the fluid passageway, the separator element comprising at least one curved section with a central rib and at least one arcuate rib on an outer side of the central rib along the curved section that curves in a direction opposite thereto.

2. A thermal pack as claimed in claim 1, wherein the separator element comprises a turn guide that directs fluid flow around the at least one turn of the fluid passageway.

3. A thermal pack as claimed in claim 2, wherein the turn guide is located adjacent an internal portion of the turn of the fluid passageway.

4. A thermal pack as claimed in claim 2, wherein the separator element further comprises a central rib which cooperates with the turn guide to provide a curved fluid channel for fluid to flow therein and around the curve of the fluid passageway.

5. A thermal pack according to claim 1, wherein at least some of the arcuate ribs are upstanding from the base adjacent to the edges of the base, a centrally extending rib being disposed between spaced pairs of arcuate ribs, wherein the each pair of arcuate ribs together with the centrally extending rib creates restricted passages at spaced locations along the track.

6. A thermal pack according to claim 5, wherein the separator element comprises at least one curved section having a turn guide extending parallel to the centrally extending rib and on an inner side thereof, such that the turn guide and centrally extending rib together provide a curved fluid channel for fluid flow around the inside curve of the track.

7. A thermal pack according to claim 6, wherein the curved section comprises a series of spaced cross-ribs extending outwardly from and perpendicular to the centrally extending rib.

8. A thermal pack according to claim 7, wherein a pair of the arcuate ribs are disposed between each successive cross-rib.

9. A thermal pack according to claim 1, wherein the separator element comprises at least one curved section with a central rib and a series of spaced cross-ribs extending outwardly from and perpendicular to the central rib.

10. A thermal pack according to claim 9, wherein the disruptors further comprise an arcuate rib disposed between each successive cross-rib.

11. A thermal pack according to claim 1, wherein the ribs comprise a central rib and a series of spaced cross-ribs extending perpendicularly from the central rib.

12. A thermal pack according to claim 11, wherein the ribs further comprise an arcuate rib disposed between each successive cross-rib.

13. A thermal pack for therapeutic treatment of a mammal, the pack comprising:
   a flexible, heat conductive liquid impermeable bladder and
   a separator,
   the bladder comprising an inlet, an outlet, and a pair of superposed sheets secured together so as to provide a fluid passageway having a turn therein,
   the separator comprising a length and a lateral width and a fluid conveying track, the separator being received within the fluid passageway and extending along its length and throughout the fluid passageway substantially from the inlet to the outlet to maintain the superposed sheets in spaced apart relationship at least in the vicinity of the track to mitigate restrictions in the fluid flow through the passageway when the pack is flexed, in use, out of the plane of the superposed sheets, the separator comprising a strip of flexible material having a base and a plurality of ribs upstanding perpendicularly from the base to describe therebetween the fluid conveying track, wherein two or more of the ribs are spaced from one another in a fluid flow direction and at least one of the ribs is arcuate in form and curves in a direction opposite to the turn such that a part thereof extends in a lateral direction so as to deflect fluid flow out of the fluid conveying track and into the fluid passageway along one of the turns of the fluid passageway.

14. A thermal pack for therapeutic treatment of a mammal, the pack comprising:

a flexible, heat conductive liquid impermeable bladder and a separator, the bladder comprising an inlet, an outlet, and a pair of superposed sheets secured together so as to provide a fluid passageway having a turn therein, the separator comprising a length and a lateral width and a fluid conveying track, the separator being received within the fluid passageway and extending along its length and throughout the fluid passageway substantially from the inlet to the outlet to maintain the superposed sheets in spaced apart relationship at least in the vicinity of the track to mitigate restrictions in the fluid flow through the passageway when the pack is flexed, in use, out of the plane of the superposed sheets, the separator comprising a strip of flexible material having a base and a plurality of ribs upstanding perpendicularly from the base to describe therebetween the fluid conveying track, two or more of the ribs being spaced from one another in a fluid flow direction, wherein the plurality of ribs comprises a central rib extending along the separator and at least one of the ribs is a cross-rib extending perpendicularly from the central rib so as to extend in a lateral direction to deflect fluid flow out of the fluid conveying track and into the fluid passageway along one of the turns of the fluid passageway.

15. A thermal pack according to claim 14, wherein the central rib is interrupted.

16. A thermal pack according to claim 15, wherein the plurality of ribs comprises a plurality of cross-rib pairs each including a cross-rib extending perpendicularly and outwardly from each side of the interrupted central rib to provide a plurality of spaced cruciform shaped ribs.

17. A thermal pack according to claim 15, wherein the plurality of ribs comprises arcuate ribs disposed between each successive cross-rib.

18. A thermal pack according to claim 14, wherein the central rib is one of a pair of central ribs, each central rib comprising a plurality of cross-ribs extending perpendicularly and outwardly therefrom.

19. A thermal pack according to claim 18, wherein the plurality of ribs comprises a plurality of spaced cross-ribs extending perpendicularly from the central rib and a straight rib disposed between each successive cross-rib.

20. A thermal pack according to claim 18, wherein the plurality of ribs comprises a plurality of spaced cross-ribs extending perpendicularly from the central rib and an arcuate rib disposed between each successive cross-rib.

* * * * *